United States Patent [19]
Bauman

[11] Patent Number: 5,485,840
[45] Date of Patent: Jan. 23, 1996

[54] METHOD OF PRECISE GUIDANCE FOR DIRECTIONAL ATHERECTOMY USING ULTRASOUND

[76] Inventor: Robert P. Bauman, 211 Kirkwood Dr., Chapel Hill, N.C. 27514

[21] Appl. No.: 213,216

[22] Filed: Mar. 15, 1994

[51] Int. Cl.$^6$ ....................................... A61B 8/12
[52] U.S. Cl. ....................................... 128/660.03
[58] Field of Search ............................. 128/658, 660.03, 128/662.06, 916; 606/159, 180, 194

[56] References Cited

U.S. PATENT DOCUMENTS

| | | | |
|---|---|---|---|
| 4,794,931 | 1/1989 | Yock | 128/660.03 |
| 5,000,185 | 3/1991 | Yock | 128/662.03 |
| 5,029,588 | 7/1991 | Yock et al. | 128/662.06 |
| 5,054,492 | 10/1991 | Scribner et al. | 128/662.06 |
| 5,095,911 | 3/1992 | Pomeranz | 128/662.06 |
| 5,100,424 | 3/1992 | Jang et al. | 606/159 |
| 5,181,920 | 1/1993 | Mueller et al. | 606/159 |
| 5,203,777 | 4/1993 | Lee | 128/658 X |
| 5,209,749 | 5/1993 | Buelna | 128/658 X |
| 5,312,427 | 5/1994 | Shturman | 606/159 X |
| 5,353,798 | 10/1994 | Sieben | 128/662.06 |
| 5,361,768 | 11/1994 | Webler et al. | 128/662.06 X |
| 5,383,460 | 1/1995 | Jang et al. | 128/662.06 X |

Primary Examiner—Francis Jaworski
Attorney, Agent, or Firm—Linda M. Deschere

[57] ABSTRACT

An improved method of performing atherectomy on plaque material at a site within a vessel utilizing a directional atherectomy catheter with a cutter which has a marker such as a cutter window which is visualizable on fluoroscopy and which is used to direct cuts, and an ultrasonic imaging apparatus. The method includes positioning the catheter cutter with fluoroscopy such that the directional marker is perpendicular to the X-ray beam; making an initial reference cut in the plaque material in the vessel; utilizing the ultrasonic imaging apparatus locate the initial reference cut to orient the distribution of plaque with respect to the visualized position of the fluoroscopically visualized directional marker on the cutter so that subsequent cuts made with the cutter result in plaque removal in an area having a predetermined spatial relationship to the initial reference cut; performing a first series of organized cuts of said plaque including making one or more passes with the cutter in said area; ultrasonically visualizing said vessel to determine the remaining location of plaque after said first series of organized cuts; performing additional cuts in said area and ultrasonically visualizing the vessel until all of the plaque in the area is removed, or the amount removed is judged to be appropriate by the operator; followed by repeated additional cuts of said plaque at additional chosen areas and ultrasonic visualization thereof.

12 Claims, 3 Drawing Sheets

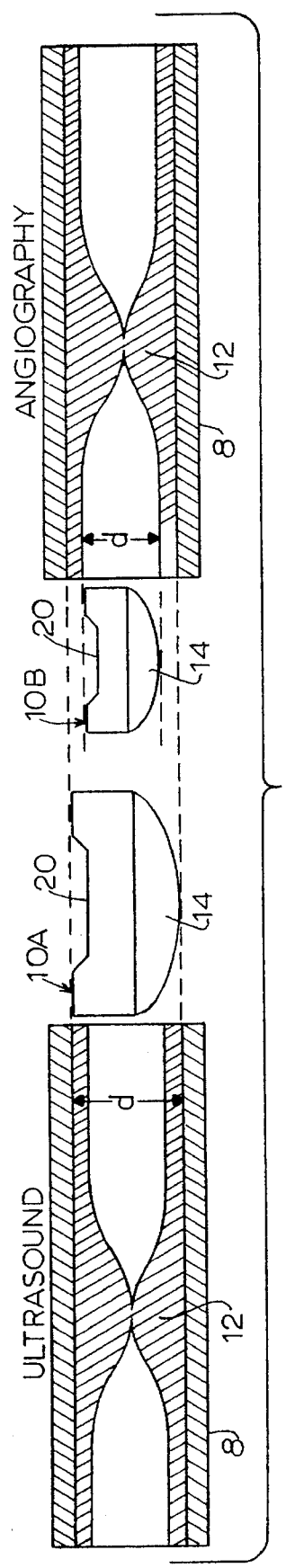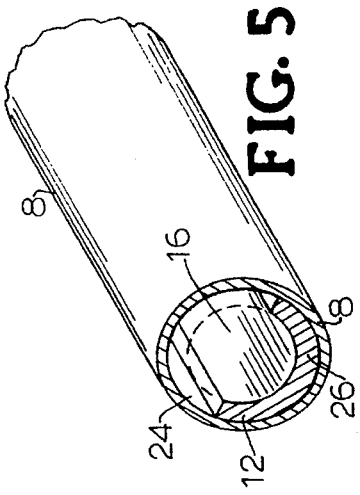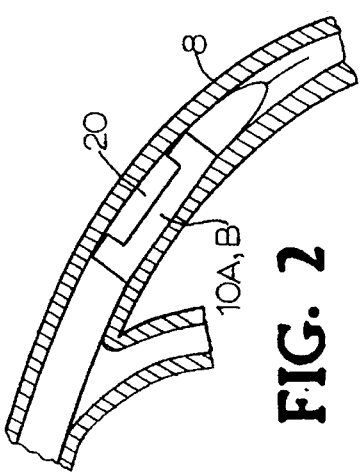

METHOD OF PRECISE GUIDANCE FOR DIRECTIONAL ATHERECTOMY USING ULTRASOUND

BACKGROUND OF THE INVENTION

1. Field of the Invention

This invention relates to methods for removing atherosclerotic plaque, and in particular, pertains to a method of precise guidance for directional atherectomy for more complete removal of plaque.

2. Description of the Related Art

Angiography is the visualization of blood vessels after injection of a radiopaque substance. Angiography is often used to show the location and number of plaque sites, as well as the length of the plaque area and the severity of the plaque problem. In addition, angiography may be used prior to atherectomy to measure the lumen diameter inside the accumulated plaque in the vessel. The plaque cutter size is normally chosen to fit within this lumen to minimize the likelihood of perforation of the vessel wall, since angiography does not allow one to determine the actual interior dimensions of the vessel itself. The previous inability to detect appropriate removal of atherosclerotic plaque from the coronary vessel wall using angiography has been a limiting factor in the use of many atherectomy devices.

After the plaque location is known, plaque removal from blood vessels is generally accomplished using atherectomy. Many types of device for performing atherectomy have been devised.

A basic atherectomy catheter device (U.S. Pat. No. 4,411,055 of Simpson and Robert) utilizes a guiding catheter assembly in which a first tubular member is encased by a second tubular member. A dilating catheter assembly can be inserted into the guiding catheter assembly. U.S. Pat. No. 4,669,469 of Gifford and Simpson discloses a cutter mounted in a cylindrical housing which has a single luminal opening, and a flexible drive cable. An inflatable balloon is positioned outside the housing opposite the cutout, and a medium for inflating the balloon is introduced through the luminal opening of the catheter.

The blade for doing the cutting may be simply positioned in the tip of a vascular catheter to be extendable transversely when the catheter is in the correct position (U.S. Pat. No. 5,053,044 of Mueller et al.). Cutters for atherectomy devices include helical cutting blades (for example, U.S. Pat. No. 5,226,909 of Evans et al.), rotatable cylindrical cutting heads (U.S. Pat. No. 5,242,460 of Klein et al.).

The atherectomy device of Simpson (U.S. Pat. No. 4,979,951) has a generally cylindrical, relatively rigid housing with rounded distal and proximal end portions. The housing has a longitudinal cutout, inside which is disposed an atheroma cutter. A flexible drive cable extends through the flexible guide, and is connected to the atheroma cutter for operation of the atheroma cutter.

The catheter of Gifford et al. (U.S. Pat. No. 4,926,858) has a distal cutter assembly and a proximal actuator assembly for imparting both rotary and axial movement to the cutter. A retention member carried by a guide wire is positioned in front of the cutter and forms a cap to retain collected atheroma materials.

The patent of Mueller et al., U.S. Pat. No. 5,181,920, is for a device with an elongated flexible tubular member with a distal cutting assembly and having a flexible drive means within the tubular member which has a distal cutter. An inflatable dilation balloon is carried by the tubular member proximal of the cutter so that a stenosis may be dilated immediately prior to or after cutting the stenosis. Numerous balloon configurations for catheters have been devised. See, for example, U.S. Pat. Nos. 4,748,982 of Horzewski et al.; 5,092,873 of Simpson and Muller; 5,041,089 of Muller et al.; and 5,117,831 of Jang et al.

The vascular catheters used for atherectomy utilize various guide wire systems for introducing the catheters into the vascular systems. See, for example, U.S. Pat. Nos. 5,040,548 and 5,061,273 of Yock; U.S. Pat. No. 5,269,793 of Simpson; and U.S. Pat. No. 5,201,316 of Pomeranz et al.

For use of most types of cutter, fluoroscopy using X-rays allows visualization of the radiopaque cutter used to remove plaque formations. The cutter may be rotated while viewing with fluoroscopy to optimize the position of the cutter with respect to the plaque location.

Ultrasound allows visualization of the cross-section of the plaque. Ultrasound imaging catheters allow over-the-wire imaging of the catheter as the cutting process proceeds. Thus, one ultrasonic apparatus of Yock (U.S. Pat. Nos. 4,794,931 and 5,000,185) includes an ultrasonic transducer carried by the distal end of a catheter. Either the transducer or another element is rotated or translated relative to the catheter to image different portions of the vessel for intravascular imaging. A fixed ultrasonic transducer may be used to direct ultrasonic energy at a reflective surface on a rotating element which allows the interior of the blood vessel to be scanned prior to the application of laser energy to ablate the obstruction (U.S. Pat. No. 5,029,588 of Yock et al.).

The ultrasonic imaging catheter of Scribner et al. (U.S. Pat. No. 5,054,492) comprises a catheter body with an ultrasonic imaging transducer located within the distal end, and arranged to produce an image in an image plane which is normal to the axial direction of the catheter. An ultrasonically opaque element is attached to the catheter body and disposed through the image plane so that an image marker appears on the resulting ultrasonic image, corresponding to the location on the catheter where the element is located, relative to a fluoroscopic marker on the catheter itself. This allows the actual rotational orientation of the catheter within the body lumen being viewed to be known.

An ultrasonic imaging means may be affixed to an abrasive rotatable head which is used for removal of intravascular plaque (U.S. Pat. No. 5,100,424 of Jang et al.). Other ultrasonic imaging systems include, for example, U.S. Pat. No. 5,203,338 of Jang; U.S. Pat. No. 5,209,235 of Brisken et al.

Although ultrasound is potentially well suited to augment angiography in guiding directional atherectomy, the orientation of cuts based on identification of branch vessels common to both the ultrasound and the angiographic images lack precision and can be quite time-consuming. Although ultrasonic imaging allows visualization of the interior of the actual vessel, even if the vessel has an interior plaque layer, and fluoroscopy allows visualization of the cutter, it is not possible to view both the plaque and the cutter as the cutter is operated. Therefore, it is difficult to perform the cutting accurately so that the desired quantity of plaque is removed without perforation of the vessel wall. Because the plaque may be uneven, or the cutting may begin off-center of the vessel, even very gradual removal of plaque in a gradually increasing circle around the apparent vessel center may result in perforation of the vessel on one side of the vessel before plaque is entirely removed.

It is therefore an object of this invention to provide a method of visualizing plaque removal as the removal process proceeds to allow substantial plaque removal from the vessel at minimal risk of wall perforation.

It is a further object of this invention to provide a method of determining cutter size based on actual vessel size (the size of the vessel without the plaque) rather than on plaque lumen size and utilizing larger cutters sized to the actual vessel size, without increasing the likelihood of vessel wall perforation during the plaque removal process, which is contrary to what would be expected with the use of a larger cutter.

It is a further object of this invention to provide a method of removing plaque which combines the strengths of both angiography and ultrasound imaging to more effectively guide directional atherectomy for more complete removal of plaque from native coronary arteries.

It is a further object of this invention to provide a method which allows about 90% plaque removal from outside the body using atherectomy catheters for essentially any vessel without increased risk of perforation or with decreased risk of perforation.

Other objects and advantages will be more fully apparent from the following disclosure and appended claims.

SUMMARY OF THE INVENTION

The invention is a new and reproducible method which maximizes the removal of atherosclerotic plaque without perforation using directional atherectomy, and includes use of intravascular ultrasound to select the cutter size which will span the media to media diameter of the vessel. The method combines the strengths of both angiography and ultrasound to more effectively guide directional atherectomy based on making a reference cut to orient the distribution of plaque to the position of the cutter window on fluoroscopy and thereby directing each series of cuts toward residual plaque and away from regions without plaque. The method of the invention minimizes inflation pressures to reduce the dilating effect and the possibility of perforation.

The invention is thus an improved method of performing atherectomy on plaque material at a site within a vessel utilizing a directional atherectomy catheter with a cutter which has a marker (preferably a cutter window) which is visualizable on fluoroscopy and which is used to direct cuts. The method comprises positioning the catheter cutter with fluoroscopy such that the directional marker is perpendicular to the X-ray beam; making an initial reference cut in the plaque material in the vessel; utilizing an ultrasonic imaging apparatus to locate the initial reference cut to orient (map) the distribution of plaque with respect to the visualized position of the fluoroscopically visualized directional marker on the cutter so that subsequent cuts made with the cutter result in plaque removal in a first area having a predetermined spatial relationship to the initial reference cut; performing a first series of organized cuts of said plaque including making one or more passes with the cutter in the first area; ultrasonically visualizing said vessel to determine the remaining location of plaque after said first series of organized cuts; performing additional cuts in the first area and ultrasonically visualizing the vessel until all of the plaque in the first area is removed, or the amount removed is judged to be appropriate by the operator.

These cuts are followed by repeatedly performing additional cuts of said plaque at additional chosen areas of the site which have a predetermined spatial relationship to the initial reference cut and to the first series of organized cuts, and ultrasonically visualizing the vessel to determine the location of residual plaque after the additional cuts.

In the preferred embodiment, the cuts performed after the reference cut are located in a 180° arc centered about the reference cut, with said cuts being done in a first hemicylindrical area of the plaque until all plaque is removed or the amount removed is judged to be appropriate by the operator. In the preferred embodiment, later cuts are performed in the remaining hemicylindrical area of the plaque until that area is sufficiently clear of plaque.

The method of the invention allows atherectomy to be performed utilizing a balloon pressurized at a very low initial pressure, for example, a pressure of about 7.5 pounds per square inch to hold the cutter against the plaque material.

Other aspects and features of the invention will be more fully apparent from the following disclosure and appended claims.

BRIEF DESCRIPTION OF THE DRAWINGS

FIG. 1 is a schematic diagram of how cutter devices may be sized for use in atherectomy.

FIG. 2 is a schematic side-view of a cutter device in a vessel.

FIG. 5 is a perspective view of hemicylindrical removal of plaque.

DETAILED DESCRIPTION OF THE INVENTION AND PREFERRED EMBODIMENTS THEREOF

Figure 3A:
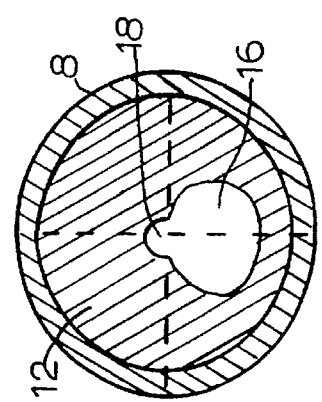
FIG. 3A is a cross-sectional view of a vessel in which a reference cut (RC) has been made in the plaque.

The invention herein is an improved method of performing atherectomy on plaque material at a site within a vessel utilizing a directional atherectomy catheter with a cutter which has a marker which is visualizable on fluoroscopy. The preferred marker is a cutter window. Examples of cutters which may be utilized in the invention include the SIMPSON ATHEROCATH™ or the SCA-EX™ manufactured by Devices for Vascular Intervention (Redwood, Calif.). Any other directional atherectomy catheter with any type of cutter may be used in the invention so long as it has a marker which can be visualized when within the vessel, such as by fluoroscopy. The marker on the cutter is used to direct cuts in traditional atherectomy, and in the invention herein.

Also utilized in the method of the invention is an ultrasonic imaging apparatus. Such apparatuses are typically known in the art as separate from atherectomy catheters. The method could still be used with combination devices should such be devised, so long as the cutter marker could be visualized as discussed above, and all or nearly all of the plaque (e.g., 300–360 degrees) could be visualized with the ultrasonic imaging. The invention, however, allows optimal use of these two devices even though not combined, by alternation of periods of use following making of the initial reference cut.

The method of the invention comprises positioning the catheter cutter with fluoroscopy such that the directional marker is perpendicular to the X-ray beam from the fluoroscope. After the catheter cutter is positioned, an initial reference cut is made in the plaque material in the vessel. Utilizing the ultrasonic imaging apparatus, the initial reference cut is located to orient or map the distribution of plaque with respect to the visualized position of the fluoroscopically visualized directional marker on the cutter so that subsequent cuts made with the cutter result in plaque removal in a first area having a predetermined spatial relationship to the initial reference cut as discussed in more detail below.

A first series of organized cuts of said plaque is performed by making one or more passes with the cutter in the first area. The term "organized cuts" as used herein means that the cuts are done in a preselected area chosen with respect to the reference cut, and any other cuts which have been done, which is in turn preferably chosen based on where the plaque is thickest in the vessel. The vessel is ultrasonically visualized to determine the remaining location of plaque after said first series of organized cuts. Additional cuts are performed in the first area and the vessel is again ultrasonically visualized until all of the plaque in the first area is removed, or the amount removed is judged to be appropriate by the operator. The operator then repeatedly performs additional cuts of said plaque at additional chosen areas of the site which have a predetermined spatial relationship to the initial reference cut and to the first series of organized cuts and ultrasonically visualizes the vessel to determine the location of residual plaque after the additional cuts.

Preferably the cutter which is used in the method of the invention is selected based on a determination of the actual interior dimensions of the vessel itself using an ultrasonic image of the vessel prior to atherectomy and non on the size of the lumen within the plaque.

Referring now to the Figures, FIG. 1 shows how either angiography or ultrasound may be used to size cutters for atherectomy. As illustrated on the left-hand side of FIG. 1, when ultrasound is used, sizing of the atherectomy catheter device maximizes the size of cutter 10A that can be used by providing information on the actual internal diameter of the vessel inside the walls 8 and not inside the plaque 12. This allows complete removal of plaque 12 because the device spans the media to media diameter when the balloon 14 is inflated. In contrast, the right side of FIG. 1 demonstrates the potential disadvantage of angiography in that the lumen 16 of the reference segment of the coronary artery may be narrowed by plaque 12. This can lead to undersizing of the cutter device 10B in relation to the media to media diameter when angiography is used. Vessel diameter and the respective cutter sizes typically used in the method of the invention are: cutter size 5F: 2.5–2.9 mm; cutter size 6F: 3.0–3.4 mm; cutter size 7F: 3.5–3.9 mm and cutter size 7FG: greater than or equal to 4.0 mm.

The method of the invention of guiding directional atherectomy uses the atherectomy device to create points of reference common to both the ultrasound and fluoroscopy images to guide subsequent cuts. The method begins with a single reference cut (FIG. 3A). Although a single reference cut is the preferred embodiment of the invention, the invention also contemplates that multiple reference cuts may be used, so long as the operator can clearly distinguish these cuts. To make the reference cut, the atherectomy catheter device is positioned so that the cutter spans the stenosis and is rotated until the cutter window 20 (or other marker, depending on the actual device used) is best visualized on fluoroscopy, with the opening or other marker oriented perpendicular to the X-ray beam (FIG. 2).

The balloon is inflated to sufficient pressure to allow cuts in the plaque to be made. Because the preferred embodiment of the invention utilizes ultrasound to select the cutter as discussed above, actual use of the invention has shown that a balloon inflation pressure of 7.5 pounds per square inch (psi), which is ½ atmosphere, is sufficient with the invention. This is substantially less pressure than is typically required with previous methods.

In the preferred embodiment, a single pass is made with the cutter, which marks the position of the cutter window on the surface of the plaque (FIG. 3A). The atherectomy catheter is then replaced by the ultrasound catheter. Ultrasound imaging of the reference cut orients the distribution of plaque with respect to the position of the cutter window.

Figure 3B:
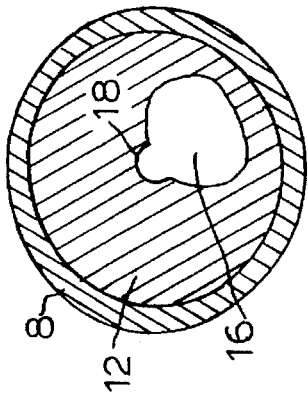
FIG. 3B is a cross-sectional view of the vessel of FIG. 3A oriented with the reference cut uppermost, and showing the quadrants (halves of the hemicylinders) of the vessel oriented with respect to the reference cut.

The ultrasound image can be rotated electronically on the monitor if desired to achieve visual alignment of the reference cut in the plaque with the fluoroscopic position of the cutter window during the reference cut (FIG. 3B). The ultrasound identifies regions where the plaque is less than 1 mm thick and there is a risk of perforation if a large cutter device is wedged in the vessel early in the cutting sequence. Directing initial cuts toward regions with more than 1 mm of thickness of plaque decompresses the plaque mass and permits safe cutting in regions with 1 mm or less of plaque.

Following the reference cut, the atherectomy is performed using the standard method of 4–8 passes with the cutter followed by removal of the device for emptying of removed plaque material. The ultrasound catheter is advanced during this emptying procedure to image the remodeled lumen and the distribution of residual plaque.

Figure 4A:
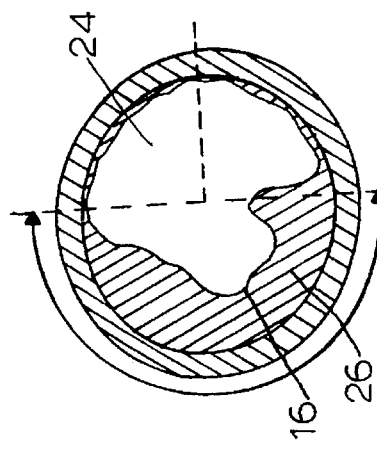
FIG. 4A is a cross-sectional view of a vessel showing the reference cut uppermost, and indicating one hemicylinder of the plaque with a double-headed arrow.

All the cuts are directed initially in a first area having a predetermined spatial relationship to the initial reference cut. In the preferred embodiment, all cuts are directed initially in a 180-degree arc 22 centered on the reference cut 18 as shown in FIG. 4A to form an elongated hemicylinder 24 of partially or completely cut plaque which opposes an elongated hemicylinder 26 of uncut plaque when the vessel is viewed three-dimensionally (FIG. 5).

As used herein the term "hemicylinder" or "elongated hemicylinder" means an area from which plaque is to be or has been removed, which has the shape which is formed when a hollow cylinder is cut in half along its linear axis (parallel to the length of the cylinder and through the central linear axis of the cylinder). The thickness of the walls of each hemicylinder of plaque which is removed may be variable and/or uneven if the lumen of the open channel of the vessel through the plaque is off center and/or is uneven in shape. The first hemicylinder which is cut preferably thus includes the thickest area of plaque, and is the area where the reference cut is made, as discussed above, to minimize the likelihood of accidental perforation of the wall.

Figure 4B:
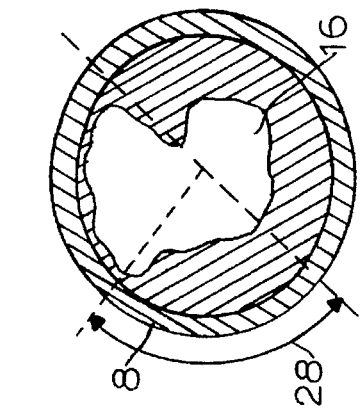
FIG. 4B is a cross-sectional view of the vessel of FIG. 4A without orienting the reference cut to be uppermost, after the plaque has been cut in half of the hemicylinder marked in FIG. 4A, with the plaque removal being in a 90-degree arc to one side of the reference cut.

An imaginary line separating these opposing hemicylinders on the ultrasound image forms a base from which to orient residual plaque in the partially cut hemicylinder to either right or left of the reference cut. Thus, in FIG. 4B cuts are shown in a 90-degree arc 28 (one half of a hemicylinder) on one side of the reference cut 18. In this manner, additional cuts are guided toward residual plaque and away from regions where the plaque has been removed to the border of the media of the vessel. This sequence of atherectomy followed by ultrasound imaging of residual plaque is continued until the initial hemicylinder is essentially clear of plaque (preferably with equal areas cleared on each side of the reference cut).

Figure 4C:
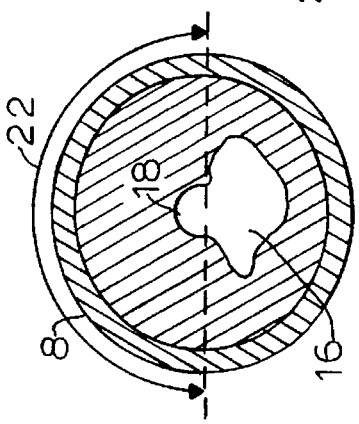
FIG. 4C is a cross-sectional view of the vessel of FIG. 4B after the entire hemicylinder (90 degrees on each side of the reference cut) has been cut.

In a similar manner, plaque is removed from the opposing uncut hemicylinder 26 (the cross-section of which is shown by the arrow in FIG. 4C). Cuts are directed in a 180-degree arc centered on a reference point 180 degrees from the reference cut. The same imaginary line separating the opposing hemicylinders on the ultrasound image orients residual plaque to either right or left of the new center point 180 degrees from the reference cut (directly across the lumen from the original reference cut in the preferred embodiment).

Although the preferred invention utilizes one reference cut and hemicylinder cuts (quarter cylinder followed by quarter cylinder), it is clear that other patterns of cutting can be employed. The important characteristics of the invention are that at least one reference cut is employed, and that subsequent cuts are organized in spatial relation to the reference cut so that it is always clear where the cutting is occurring with respect to the reference cut(s) and with respect to the thin and thick areas of plaque.

In the preferred embodiment of the invention, balloon inflation pressures begin at ½ atmosphere (7.5 psi) and are advanced in increments of ½ atmosphere up to a maximum of two atmospheres (30 psi). Typically plaque is removed completely in the reference cut hemicylinder and partially in the opposing hemicylinder with a balloon inflation of 7.5 psi. As the lumen is enlarged, higher pressures are required for the balloon to fill the space. Generally the method of the invention does not require use of any pressures greater than two atmospheres to cut the plaque. The avoidance of higher pressures may reduce the possibility of dissecting a thinned vessel wall and minimize pathologic stretching of the vessel wall.

The features and advantages of the present invention will be more clearly understood by reference to the following example, which is not to be construed as limiting the invention.

EXAMPLE

Figure 6:
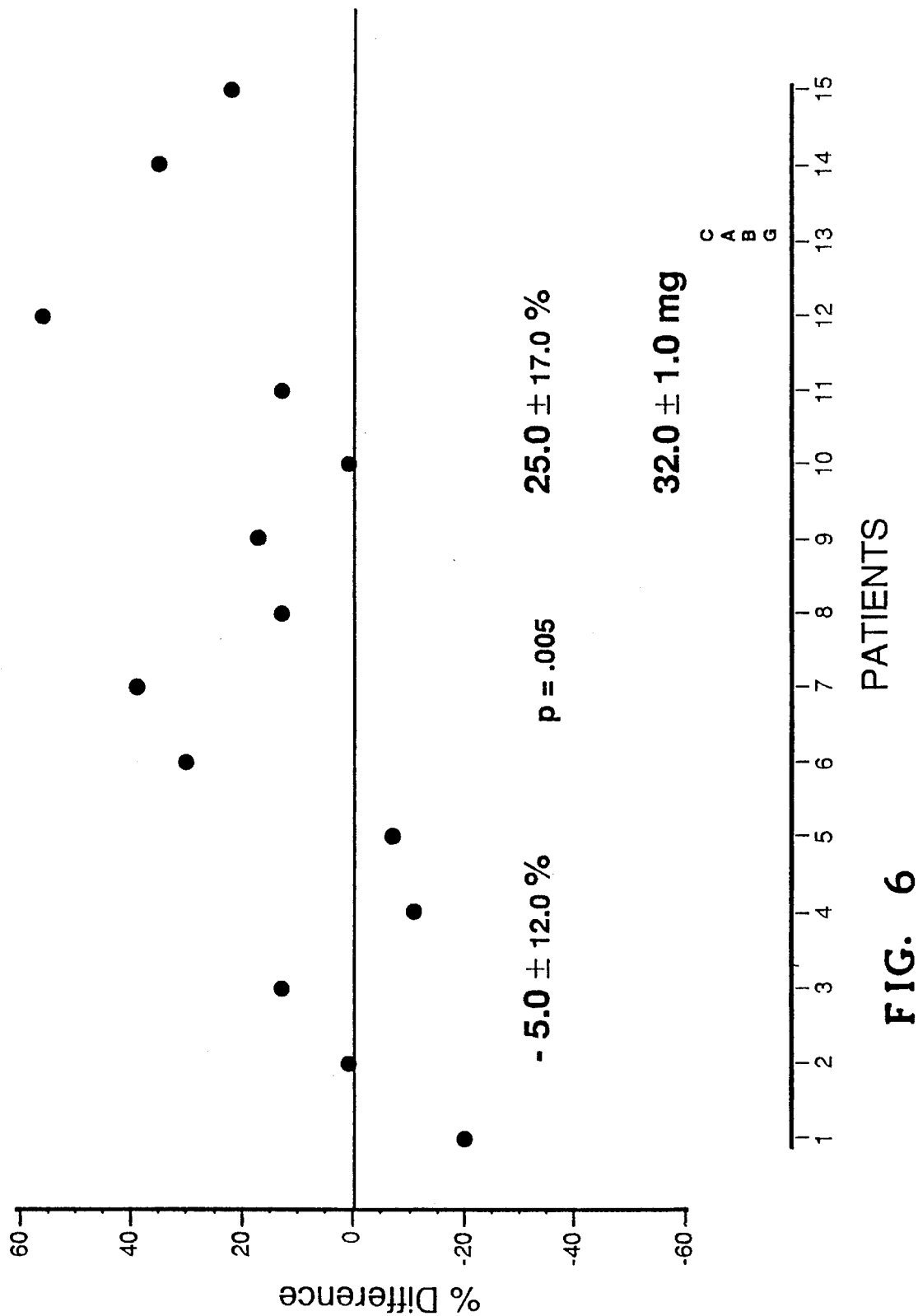
FIG. 6 is a graph of the per cent difference between mean lumen diameters of the patients' treated and control segments post atherectomy.

In a pilot study, 15 patients underwent directional coronary atherectomy with ultrasound guidance. Cutter size was upgraded from that indicated by angiography in 11 of 15 patients based on the ultrasound measurements, instead of the angiographic measurements. Lumen diameters were measured from digitized angiographic images using an automated edge detection program. Atherectomy was successful in 14 of the 15 patients. (The unsuccessful patient required coronary artery bypass grafting for a non resectable dissection flap.) There were no perforations in any of the patients. FIG. 6 shows the percent difference between the mean lumen diameters of the treated segments and the control segments post atherectomy. Post atherectomy lumens which are larger than the control are plotted above the line, and those which are less are plotted below the line. The first five patients did not have the reference cut of the invention, and the remaining patients had the reference cut of the invention. The mean percent difference±the standard deviation for the five patients without the reference cut was $-5 \pm 12$ and for the ten patients with the reference cut was $25 \pm 17$. These results differed at the level of $p=0.005$. The mean weight±standard deviation of the recovered tissue from the patients with the new method using the reference cut was $32 \pm 1$ mg.

In one case where an undersized cutter was used, an inflation pressure exceeding 30 psi was utilized to attempt to compensate for the undersized cutter. Ultrasound and angiographic imaging of the vessel after making cuts at 30 psi, and after subsequent cuts at 45 psi, did not result in additional plaque retrieval and the media to media dimension was markedly dilated from 4.6 to 6.9 mm. This change was attributed to pathologic expansion of the vessel wall, and no additional cuts were made. Inflation pressures greater than 30 psi were not used for any subsequent patients.

The experimental results indicate that large cutters can be used in the method of the invention without perforation and with a resulting large lumen which is effectively cleaned of residual plaque.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. A method of performing atherectomy on plaque material at a site within a vessel utilizing a directional atherectomy catheter with a cutter which has a marker which is visualizable with fluoroscopy utilizing an X-ray beam, and which may be used to direct cuts; and an ultrasonic imaging apparatus, said method comprising:

(a) positioning the catheter cutter with fluoroscopy in the vessel such that the directional marker is perpendicular to the X-ray beam;

(b) making an initial reference cut in the plaque material in the vessel;

(c) utilizing the ultrasonic imaging apparatus to locate the initial reference cut to orient the distribution of plaque with respect to the visualized position of the fluoroscopically visualizable directional marker on the cutter window so that subsequent cuts made with the cutter result in plaque removal in a first area having a predetermined spatial relationship to the initial reference cut;

(d) performing a first series of organized cuts of said plaque in said first area, said series of organized cuts comprising one or more passes with the cutter in said first area;

(e) ultrasonically visualizing said vessel to determine the remaining location of plaque after said first series of organized cuts;

(f) performing additional cuts in said first area followed by repetition of step (e) until a desired amount of plaque has been removed in said first area;

(g) performing cuts of said plaque at an additional chosen area of said site, said additional chosen area having a predetermined spatial relationship to the initial reference cut and to the first series of organized cuts;

(h) ultrasonically visualizing said vessel to determine the location of residual plaque after said additional cuts; and (i) performing additional cuts in said additional chosen area followed by repetition of step (h) until a predetermined desired amount of plaque has been removed from said additional chosen area.

2. The method of claim 1, further comprising repeating steps (g) through (i) until substantially all of the plaque is removed from the site.

3. The method according to claim 2, wherein said repeating steps (g) through (i) comprises:

(a) performing initial additional cuts in a 180° arc centered about the reference cut, with said cuts being done in a first hemicylindrical area; and (b) performing subsequent additional cuts in a second hemicylindrical area of the plaque which is not in the first hemicylindrical area.

4. The method according to claim 3, wherein said cuts in the first hemicylindrical area are performed first in a 90-degree segment of said plaque on a first side of the reference cut, and later cuts in the first hemicylindrical area are performed in a second 90-degree segment of the plaque on a second side of the reference cut.

5. The method according to claim 4, wherein cuts in the second hemicylindrical area are performed first in a 90-degree segment of said plaque on a first side of a point on the opposite side of the vessel from the reference cut, and later cuts in the first hemicylindrical area are performed in a second 90-degree segment of the plaque on a second side of the point on the opposite side of the vessel from the reference cut.

6. The method according to claim 1, further comprising selecting a cutter based on determination of the internal diameter of the vessel utilizing an ultrasonic image of the vessel prior to atherectomy.

7. A method according to claim 1, wherein the plaque material is thicker on a first side of the vessel lumen than on the remaining sides of said lumen, and wherein said reference cut is made in the plaque material at said first side.

8. The improved method of claim 1, further comprising utilizing a balloon pressurized at an initial pressure of about 7.5 pounds per square inch to hold the cutter against the plaque material when the cuts are made.

9. In a method of performing atherectomy on plaque material at a site within a vessel of the type utilizing a directional atherectomy catheter with a cutter which has a marker visualizable on fluoroscopy and which is used to direct cuts, and utilizing an ultrasonic imaging apparatus, the improvement comprising:

(a) making an initial reference cut in the plaque material in the vessel; and (b) utilizing the ultrasonic imaging apparatus to locate the initial reference cut to orient the position of the cutter at a first area of plaque having a predetermined spatial relationship to the initial reference cut; and (c) performing one or more of a series of organized cuts of said plaque in said first area; and (d) following each series of organized cuts of said plaque with ultrasonic visualization of the vessel to determine the remaining location of plaque.

10. The improved method of claim 9, further comprising:

(a) performing additional removal cuts of plaque material at additional chosen areas of said site in reference to said initial reference cut;

(b) ultrasonically visualizing said vessel to determine the location of residual plaque after said additional cuts;

(c) performing additional cuts in said additional chosen area followed by repetition of step 10(b) until a predetermined desired amount of plaque has been removed from said additional chosen area; and (d) repeating steps (a) through (c) until substantially all of the plaque is removed from the site.

11. The improved method of claim 9, further comprising utilizing a balloon pressurized at an initial pressure of about 7.5 pounds per square inch to hold the cutter against the plaque material while the cuts are made.

12. A method according to claim 9, wherein the plaque material is thicker on a first side of the vessel lumen on the remaining sides of the lumen, and wherein said reference cut is made in the plaque material at said first side.

* * * * *